United States Patent [19]

Rosendal

[11] Patent Number: Plant 7,224

[45] Date of Patent: May 1, 1990

[54] EXACUM PLANT NAMED BLUE ROPENDEL

[75] Inventor: Erik Rosendal, Assens, Denmark

[73] Assignee: J & L Plants, Inc., Amarillo, Tex.

[21] Appl. No.: 273,402

[22] Filed: Nov. 18, 1988

[51] Int. Cl.[5] ..... A01H 5/00

[52] U.S. Cl. ..... Plt./68

[58] Field of Search ..... Plt. 68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new cultivar of Exacum plant named Blue Ropendel having attractive single blue-violet flowers, excellent floriferousness, and a cascading growth habit.

1 Drawing Sheet

The present invention relates to a new and distinct cultivar of Exacum plant, hereinafter referred to by the cultivar name Blue Ropendel.

Blue Ropendel was discovered and selected by me as a mutation of the cultivar known as Best Blue in a controlled environment in Assens, Denmark in the Summer of 1985. The new cultivar was discovered growing among plants of the parent cultivar. It was recognized due to its trailing growth habit, as opposed to the upright growth habit of the parent cultivar Best Blue.

The first act of asexual reproduction of Blue Ropendel was accomplished by propagation from stem cuttings in Assens, Denmark in Summer of 1985. Horticultural examination of selected units, initiated in the Autumn of 1985, has demonstrated that the combination of characteristics as herein disclosed for Blue Ropendel arefirmly fixed and are retained through successive generations of asexual reproduction.

Blue Ropendel has not been observed under all possible environmental conditions. The phenotype may vary significantly with variations in environment such as temperature, light intensity and day length. The following observations, measurements and comparisons describe plants grown in Assens/Aarsley, Denmark under greenhouse conditions which approximate those generally used in commercial practice. Color references are made to The Royal Horticultural Society Colour Chart and were taken from plants grown in Denmark. The flower color of plants grown in Texas will be somewhat lighter.

The accompanying photographic drawing shows typical specimen plants of the new cultivar, grown in an 8" pot forming a hanging basket. The colors are as true as possible for color illustrations of this type. The photograph was taken in Amarillo, Tex. in Aug. 1988 under full light conditions. This accounts for the flower color appearing lighter than it actually is. The photograph is of three (3) plants of Blue Ropendel started as cuttings in an 8" pot, with the plants shown being twelve (12) weeks old.

The following traits have been repeatedly observed and are determined to be basic characteristics of Blue Ropendel, which in combination distinguish this Exacum Plant as a new and distinct cultivar:

1. Trailing growth, making the new cultivar ideally suited for hanging baskets.
2. Single flowers.
3. Attractive blue-violet flower color.
4. Easily reproduced from stem cuttings.

5. Good branching, and flexible stems.
6. Floriferous habit.

Origin: Mutation of the exacum cultivar known as Best Blue.

Blue Ropendel is primarily distinguished from its parent Best Blue by its growth habit. Whereas the parent cultivar possesses an upright growth habit and relatively rigid stems, Blue Ropendel has flexible stems and an outward as well as upward growth. This results in a cascading of the side branches so as to make the cultivar ideally suited for hanging baskets.

Plant:

1. *Form.*—Trailing or cascading, good branching.
2. *Height to flowering.*—About 15 cm.
3. *Plant diameter (mature plant).*—About 27 cm.
4. *Growth rate.*—Fast under good light conditions.
5. *Growth habit.*—Dense, cascading.
6. *Rooting time.*—About 10 to 12 days.

Foliage:

1. *Arrangement.*—Opposite, sessile leaves at the bottom of all nodes.
2. *Size.*—Leaf blade and petiole about 40 to 50 mm, length of blade about 20 to 30 mm, width about 15 to 25 mm.
3. *Base.*—Attenutate.
4. *Color.*—Petiole: near to 144B. Veins: near to 145B. Leaf top surface: near to 138A. Leaf under surface: near to 144B.
5. *Margin.*—Entire.
6. *Quantity.*—Abundant.
7. *Venation.*—Three-veined from petiole, middle vein strongest.
8. *Shape of leaves.*—Cordate to elliptic, ovate.
9. *Surface.*—Smooth.
10. *Texture.*—Glabrous.
11. *Variegation.*—None.

Stem:

1. *Color.*—Near to 144B, purplish at internodes.
2. *Length of internodes.*—about 25 to 36 mm.
3. *Breaking action.*—Sympodial.
4. *Structure.*—Strong, rounded quadrangular.

Flower:

1. *Bud color.*—Near to 145B.
2. *Bud size.*—About 5 to 6 mm.
3. *Form.*—Round.
4. *Borne.*—Terminal, single at the end of each node.

5. *Size.*—About 14 to 18 mm.
6. *Calyx.*—5-winged, color near to 143B.
7. *Petals.*—Number — 5. Top surface color — In Denmark, 87B for new to three-fourths open flowers, with flower color at same maturity in Texas being somewhat lighter, 87B-C; color fades to 87C. Undersurface color — Near to 87C. Shape — Heart-shaped.
8. *Lasting quality.*—Flowers average one week in duration.

9. *Overall appearance.*—Attractive and abundant blue-violet flowers, with fresh flowers continually replacing maturing ones.

Peduncle:

1. *Length.*—About 39 mm.
2. *Color.*—Purplish.
3. *Aspect.*—Straight.
4. *Strength.*—Erect in all directions.

I claim:

1. A new and distinct cultivar of Exacum plant named Blue Ropendel, as illustrated and described.

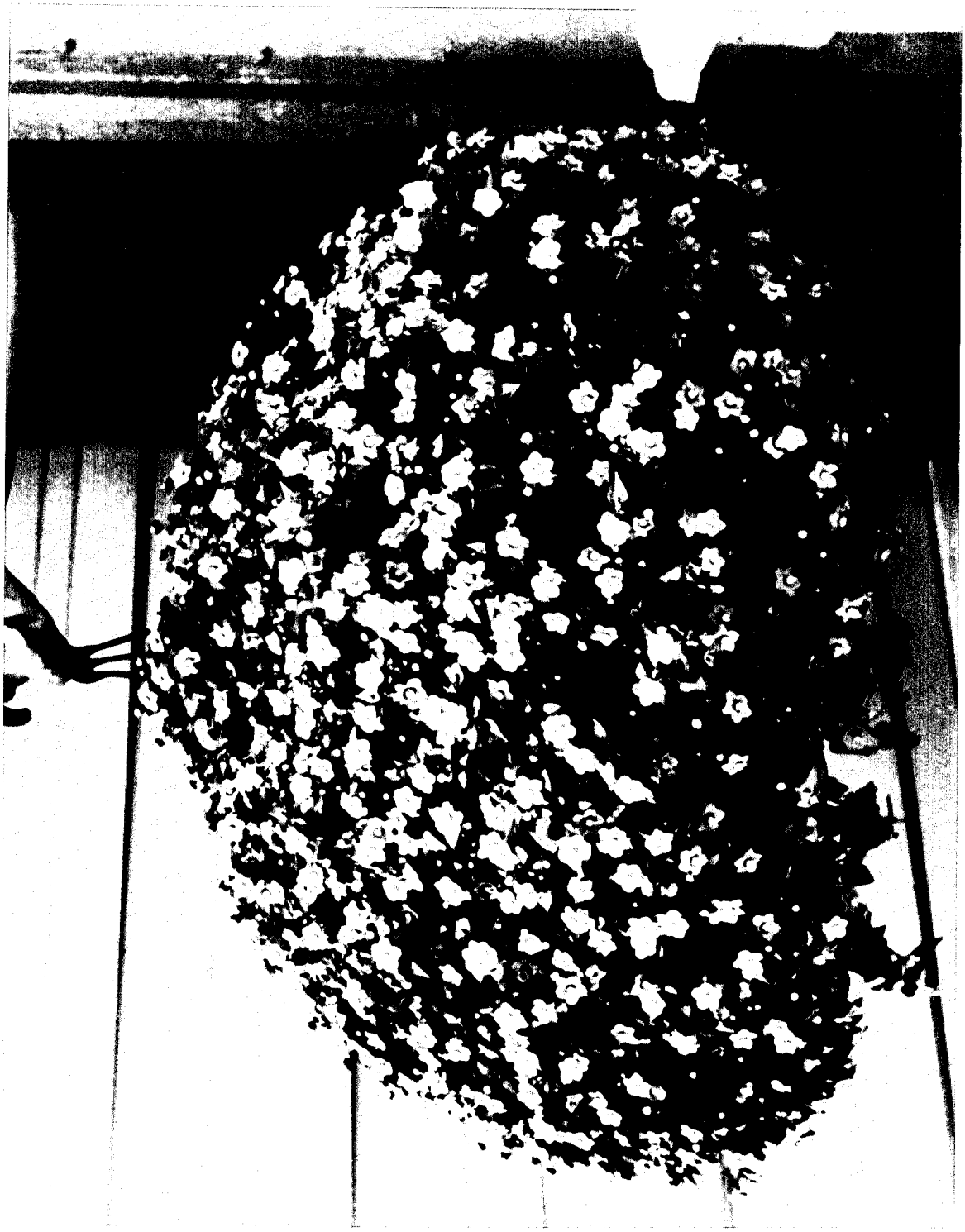

* * * * *